United States Patent [19]
Landingham

[11] Patent Number: 5,925,039
[45] Date of Patent: *Jul. 20, 1999

[54] ELECTROSURGICAL INSTRUMENT WITH CONDUCTIVE CERAMIC OR CERMET AND METHOD OF MAKING SAME

[75] Inventor: Richard L. Landingham, Livermore, Calif.

[73] Assignee: ITI Medical Technologies, Inc., Livermore, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/661,980
[22] Filed: Jun. 12, 1996
[51] Int. Cl.⁶ ..................................... A61B 17/36
[52] U.S. Cl. ............................... 606/41; 606/45
[58] Field of Search ........................... 606/41–52

[56] References Cited

U.S. PATENT DOCUMENTS

| | | |
|---|---|---|
| 4,605,440 | 8/1986 | Halverson et al. . |
| 4,674,498 | 6/1987 | Stasz . |
| 4,682,596 | 7/1987 | Bales et al. . |
| 4,718,941 | 1/1988 | Halverson et al. . |
| 4,738,248 | 4/1988 | Ray . |
| 4,802,476 | 2/1989 | Noerenberg et al. . |
| 4,850,353 | 7/1989 | Stasz et al. . |
| 4,862,890 | 9/1989 | Stasz et al. ........................... 606/48 |
| 4,922,903 | 5/1990 | Welch et al. . |
| 4,927,420 | 5/1990 | Newkirk et al. . |
| 4,958,539 | 9/1990 | Stasz et al. . |
| 5,007,908 | 4/1991 | Rydell . |
| 5,030,218 | 7/1991 | Alexander . |
| 5,071,419 | 12/1991 | Rydell et al. . |
| 5,192,280 | 3/1993 | Smith et al. . |
| 5,192,298 | 3/1993 | Parins . |
| 5,217,458 | 6/1993 | Parins . |
| 5,331,971 | 7/1994 | Bales et al. . |
| 5,342,381 | 8/1994 | Tidemand . |
| 5,395,369 | 3/1995 | McBrayer et al. . |
| 5,396,900 | 3/1995 | Slater et al. . |
| 5,697,926 | 12/1997 | Weaver . |

OTHER PUBLICATIONS

F.A. Cotton and G. Wilkinson, *Advanced Inorganic Chemistry, 5th Edition,* John Wiley & Sons (1988), pp. 234–241 and 652–665.

W.D. Kingery, *Introduction to Ceramics,* John Wiley & Sons, Inc. (1967), pp. 647–685.

*Primary Examiner*—David M. Shay
*Attorney, Agent, or Firm*—Limbach & Limbach L.L.P.

[57] ABSTRACT

An electrosurgical instrument including an active electrode surface made of a conducting ceramic or cermet. The conducting ceramic may be a carbide, boride, or nitride ceramic or a mixture of these ceramics. The cermet may include a ceramic and a metal selected from the group consisting of Cobalt, Nickel, Iron, Tungsten, Molybdenum, Titanium, Zirconium, and Aluminum. The conducting ceramic or cermet active electrode surface may be supported on a core. In some embodiments, the core is a metal core with the active electrode surface formed as a coating on a surface of the metal core. In other embodiments, the core is made of electrically insulating material. Some embodiments of the invention are Bovie blades, bipolar forceps, cauterizing end effectors for endoscopic surgery, bipolar biopsy devices, and spatula blades having the inventive active electrode surface.

35 Claims, 2 Drawing Sheets

ELECTROSURGICAL INSTRUMENT WITH CONDUCTIVE CERAMIC OR CERMET AND METHOD OF MAKING SAME

BACKGROUND

The present invention relates generally to instruments for use in electrosurgical techniques. More specifically, the invention relates to electrosurgical instruments made of conducting ceramics or cermets and the use and manufacture of these instruments.

Electrosurgery has become an important alternative to conventional surgical techniques and offers many unique advantages over the traditional procedures. In electrosurgery, an electric current is used to cut or cauterize human or animal tissue. Presently, there are two main types of electrosurgical apparatus in use. Depending on the number of electrodes used in the cutting and cauterization these instruments are called unipolar or bipolar.

In a unipolar electrosurgical apparatus, current (usually "RF" current) is supplied to an electrode which is used to cut or cauterize the tissue. When in use, current flows through the electrode to the patient and the circuit is completed using a "patient plate" on which the patient lies. The surface area of the electrode through which current flows (the "active electrode surface") is small relative to the area of the patient plate and therefore an intense local current density is generated at the electrode. This results in cutting or cauterization of the tissue in the immediate proximity of the electrode. An example of a unipolar electrosurgical instrument is described in U.S. Pat. No. 4,927,420, which is incorporated herein by reference.

In a bipolar electrosurgical apparatus, the "patient plate" of the unipolar apparatus is replaced by a second electrode separated from the first electrode by a small gap. In operation, an intense local current density is generated between the electrodes and this results in cutting or cauterization of the tissue between the electrodes. Examples of bipolar electrosurgical instruments are described in U.S. Pat. Nos. 5,396,900, 5,217,458, 5,342,381, and 5,395,369, all of which are incorporated herein by reference.

The electrodes used in both unipolar and bipolar apparatus come in a wide variety of shapes, sizes, and configurations. Depending on the surgical requirements, the electrodes can be in any of a variety of shapes such as needles, loops, spatulas, scalpel blades, scissors, forceps, and balls. Electrosurgical techniques have also been extensively used for endoscopic surgery. Since electrosurgical tools can be made much smaller than their conventional counterparts, electrosurgery is especially suited to this type of surgery. A wide variety of shapes and configurations of endoscopic electrodes have been described. See for example U.S. Pat. Nos. 5,396,900, 5,217,458, and 5,395,369.

In conventional electrosurgical instruments the active electrode surfaces are usually made of stainless steel ("SS"). However, there is a well known drawback to using such SS electrodes; namely, that burnt tissue layers adhere to the electrode surface during the electrosurgical procedure. It is thought that the mechanism that causes tissue to stick to the instruments is as follows.

During electrosurgical procedures, an intense electric current density is generated between the electrodes and the tissue. In fact, the electrosurgical procedure often causes arcing between the electrode and the tissue. The high current density causes intense heating which carburizes the tissue and results in the required cutting or cauterization. The electrodes of the conventional instruments react with this carburizing atmosphere and this forms adherent burnt tissue layers on the surface of the electrodes. During the electrosurgical procedure, burnt tissue begins to build up on the instrument surfaces in the form of a black film. When this buildup is thick enough to sufficiently reduce the current density between the electrode and the tissue, the tissue coming into direct contact with the hot black film will stick. The surgeon is then forced to stop the operation and clean the electrosurgical instrument. This cleaning can require enough force to scratch the surface of the SS. Such scratches roughen the surfaces of the instrument and this in turn causes tissue residue to build up faster and results in more sticking.

An additional drawback of the conventional instruments is that the electrosurgical procedure heats the electrodes and since SS is a relatively poor thermal conductor the instrument rapidly heats up to very high temperatures (>500° F.). Furthermore, the electrosurgical procedure also transfers some of the metal to the tissue which pits the surface of the metal electrode and contaminates the wound. The composition of the stainless steel electrodes includes iron, nickel, and chromium which may be deposited into the wound with harmful consequences. The pitting of the electrode surface also further roughens the surface and therefore exacerbates the problem of tissue buildup.

Many electrosurgical instruments also include non-conducting ceramics (used as insulating elements) in addition to metal electrodes. These ceramics are typically oxide ceramics which, in the carburizing environment present during the electrosurgical procedure, also react and form adherent tissue layers. There have been many attempts made to overcome the problem of tissue buildup in the conventional apparatus. For example, the metal electrodes have been coated with an organic material, usually a Teflon material or another polymer. Unfortunately, these low melting, volatile materials cannot withstand the high localized temperatures of the electric discharge between the electrode surface and the tissue. The resulting products of these melted/vaporized coatings are known to form harmful chemicals and undesirable products are deposited into the cut/cauterized wounds. Surgical staff have reported that after exposure to these vaporized organic coatings, flu-like symptoms result (this problem has been termed "polymer fume fever" or "teflon flu"). A further disadvantage is that a coating of organic material is melted in the very early stages of the electric discharge and therefore provides little or no improvement in the reduction of tissue adhesion. It is typical for the surface of a conventional SS electrode to be roughened (prior to conventional coating with Teflon material) to improve the mechanical bond between the SS and the coating, and in this case only a roughened metal surface remains following the initial discharge, thereby promoting increased pitting of the metal surface. This pitting also results in transfer of the metal from the electrode to the tissue.

Another proposed solution to the problem of tissue adhesion is the use of a vibrating blade. Such a solution is disclosed in U.S. Pat. Nos. 4,674,498, 4,802,476, and 4,922,903. These references describe electrosurgical apparatus including means for vibrating an electrosurgical blade during use to prevent buildup of tissue and debris on the blade. This technique requires the apparatus to include a means for vibrating and a means for coupling the vibrations to the electrosurgical instrument. This increases the cost and complexity of the apparatus and in some cases, for instance endoscopic surgery, may present great technological problems.

In U.S. Pat. No. 4,927,420 Newkirk et al. describe the use of an ultrasharp metal needle (composed of any of a variety of refractory alloys) in electrosurgery. The use of an ultrasharp needle is said to allow use of lower RF power which reduces scarring and helps eliminate drag (tissue buildup) when cutting tissue. However, the elimination of drag in using such a needle relies on being able to use reduced RF power which in turn relies on the use of an ultrasharp needle. Thus the teaching of U.S. Pat. No. 4,927,420 is severely limited in the range of shapes of electrosurgical instruments to which it may be applied.

The use of refractory metal electrodes is also disclosed by Grabinger et al. in U.S. Pat. No. 4,850,353 which describes the use of refractory metal conductive strips attached to an insulating ceramic substrate.

Ceramics have been used extensively in electrosurgical instruments, however, these materials have always been nonconducting ceramics that have specifically been used for insulating the metal electrodes. Such arrangements have been described, for example, in U.S. Pat. Nos. 4,862,890, 4,958,539, 5,071,419, 4,850,353, 5,192,280, 5,396,900 and 5,007,908. In all previous electrosurgical instruments of which the inventor is aware, the active electrode surface through which the current flows is made of metal or polymer coated metal and not ceramic.

From the foregoing discussion it is obvious that there exists a basic problem in electrosurgery; namely, the buildup of tissue on electrosurgical instruments during the electrosurgical procedure. Although some solutions to this problem have been proposed, these all have their own drawbacks. There is therefore a need for electrosurgical instruments to which tissue does not adhere, and which can be formed in a wide variety of shapes. Furthermore, there is a need for electrosurgical instruments to which tissue does not adhere and which function without the instrument being coupled to any external mechanical vibrating means.

SUMMARY OF THE INVENTION

The present invention meets the above needs by providing electrosurgical instruments that include an active electrode surface made of a conducting ceramic or cermet.

The conducting ceramic may be a carbide ceramic, boride ceramic, nitride ceramic, or a mixture of two or more of these ceramics. Suitable conducting ceramics include Boron Carbide, Tungsten Carbide, Titanium Carbide, Molybdenum Carbide, Niobium Carbide, Zirconium Carbide, Titanium Nitride, Aluminum Nitride, Titanium Boride, Zirconium Boride, Vanadium Carbide, Hafnium Carbide, and Tantalum Carbide. Optionally, these conducting ceramics may be dispersed in an insulating ceramic matrix (example: TiC in $Al_2O_3$).

The cermets may include a ceramic and a metal including Silver, Copper, Platinum, Tantalum, Vanadium, Tungsten, Titanium, Hafnium, Zirconium, Niobium, Cobalt, Nickel, Iron, Molybdenum, and Aluminum. The ceramic component may be a carbide, boride, oxide, nitride, silica or mixtures of these ceramics. The metal component may be a refractory or transition metal. Suitable cermets include Aluminum/Boron Carbide, Cobalt/Tungsten Carbide, Nickel Iron/Tungsten Carbide, Nickel Molybdenum/Titanium Carbide, Titanium/Aluminum Oxide, Aluminum/Aluminum Oxide, and an Aluminum Alloy/Boron Carbide. If the cermet is Aluminum/Boron Carbide or an Aluminum Alloy/Boron Carbide it may contain between about 40% and about 80% by weight of $B_4C$.

Optionally, the conducting ceramic or cermet active electrode surface may be supported on a support means. The support means may be a metal core in which case the active electrode surface may be formed as a coating on its surface. Alternatively, the support means may be an insulating support means.

If the conducting ceramic or cermet active electrode surface is supported on a metal core, the conducting ceramic or cermet may contain a metal component that is the same metal as the metal core. Also, the electrosurgical instrument may be fabricated by contacting the metal core with carbon, boron, nitride, or conductive ceramic/cermet mixture to produce a coating on a surface of the metal core.

The electrosurgical instrument may also include means for maintaining the active electrode surface at a desired potential.

The active electrode surface may be substantially unreactive in the carburizing environment present during electrosurgery.

BRIEF DESCRIPTION OF THE DRAWINGS

FIGS. 2b and 2c are cross-sectional views of the blade of FIG. 2a, taken respectively along line 2B—2B of FIG. 2a and line 2C—2C of FIG. 2a.

DETAILED DESCRIPTION

Figure 1A:
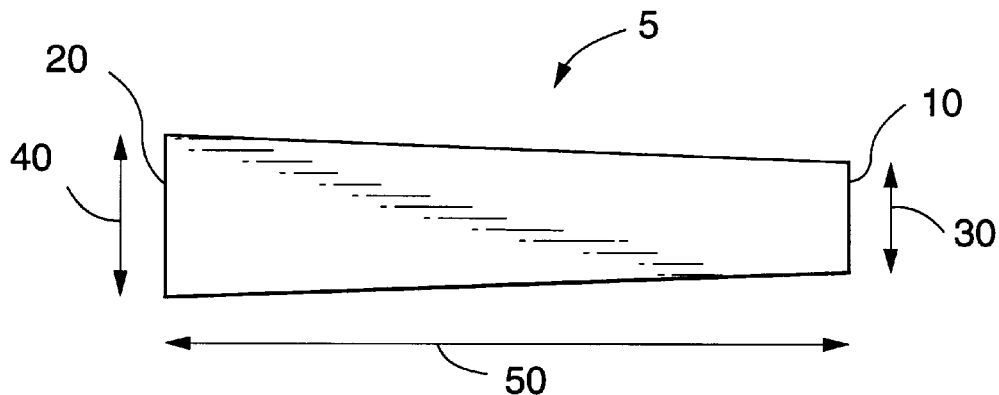
FIGS. 1a, 1b, and 1c are respectively top, side, and perspective views of a cermet electrosurgical instrument (a Bovie blade) according to the present invention.

The following definitions are provided:

Electrosurgical instrument—any surgical instrument that is used for supplying electrical current to a subject. The subject may be either animal or human. Examples of electrosurgical instruments include, but are not limited to, Bovie Blades, bipolar forceps, cauterizing end effectors (for endoscopic surgery), bipolar biopsy devices, spatula blades, ball electrodes, arthroscopic hook electrodes, L and J hook electrodes (for laparoscopic surgery), extended blade electrodes, needle electrodes, extended needle electrodes, curved electrode, angled blade electrode, and loop electrodes (for histological examinations and gynecologic tissue extractions).

Active Electrode Surface—that area of the surface of an electrosurgical instrument through which electric current is supplied to the subject.

Ceramic—A material useful for making solid articles which has as its essential component, and is composed in large part of, one or more inorganic, nonmetallic materials. Examples of such materials include refractory, covalent and most ionic bonded materials.

Conducting ceramic—a ceramic that is an electrical conductor. Specifically, a ceramic that has a large enough electrical conductivity that it may be used as an active electrode surface in an electrosurgical instrument.

Cermet—a material consisting of a mixture of ceramic and metallic components that has a large enough electrical conductivity that it may be used as an active electrode surface in an electrosurgical instrument.

Carbide, Boride, Nitride, Oxide and mixed Ceramics—ceramics that include carbon, boron, nitrogen, oxygen, or mixtures thereof, respectively. Specific ceramics are denoted by either their name or chemical formula. For example, Tungsten Carbide or WC. The chemical formula does not denote the stoichiometry of the material but merely the elemental composition. When necessary, specific stoichiometries are given.

Conducting composite ceramic—a mixture of two or more ceramic materials in which one or more of the ceramics has a large enough electrical conductivity that the composite ceramic may be used as an active electrode surface in an electrosurgical instrument.

INTRODUCTION

The inventor has discovered that the ceramics and cermets described below do not suffer from the drawbacks of the previous materials used in electrosurgical instruments; that is, they do not react in the carburizing environment and therefore do not form adherent tissue layers during the electrosurgical procedure. Furthermore, the ceramics and cermets of the present invention are conducting and so can be used as the active electrode surfaces of electrosurgical instruments.

Generally, the electrosurgical instruments of the present invention may have active electrode surfaces made from any material which is electrically conducting and does not appreciably react in the carburizing environment present during electrosurgery. More specifically, the inventor has found that one class of materials that may be used are carbide, boride, or nitride ceramic systems (or mixtures thereof). Another class of materials that may be used are cermets: compositions that include both ceramic and metal components.

It is important to note that only the surface of the electrosurgical instrument that is in contact with the carburizing environment, i.e. the active electrode surface, need be made of a non-reactive material. Therefore, so long as the active electrode surface is made of the ceramics or cermets of the present invention, the remainder of the instrument may be made of any suitable material. For instance, to improve the mechanical properties of the instrument, the materials of the present invention may be coated onto a metal core, or other supporting means. Examples of such instruments are discussed below but first we describe in detail the ceramics and cermets of the present invention.

CERAMICS

As described above, one class of materials that may be used in the present invention are carbide ceramics, boride ceramics, nitride ceramics, and mixtures of these ceramics. These materials posses many properties useful in the present invention including good electrical conductivity, good thermal conductivity, and excellent hardness properties. In fact, these ceramics are some of the hardest materials known and are resistant to scratching and pitting. Since tissue build up is increased by rough surfaces, the hardness property helps further reduce tissue sticking. Furthermore, these materials do not substantially react in the carburizing environment present in the electrosurgical procedure and therefore do not suffer from tissue buildup. We stress that the ceramics of the present invention are both unreactive to the carburizing environment and are electrically conducting. This is in direct contrast to the oxide ceramics which are used as insulating elements in conventional instruments and which may react in the carburizing atmosphere.

In one embodiment of the present invention the active electrode surface of an electrosurgical instrument may be made of a carbide ceramic, boride ceramic, nitride ceramic, and mixtures of these ceramics. Suitable ceramics include (but are not limited to) the systems of Boron Carbide ($B_4C$), Tungsten Carbide (WC), Titanium Carbide (TiC), Molybdenum Carbide (MoC), Niobium Carbide (NbC), Zirconium Carbide (ZrC), Titanium Boride ($TiB_2$), Titanium Nitride (TiN), Aluminum Nitride (AlN), Zirconium Nitride (ZrN), Zirconium Boride ($ZrB_2$), Vanadium Carbide (VC), Hafnium Carbide (HfC), and Tantalum Carbide (TaC). The most common stoichiometries for these ceramics are shown in parentheses. As is well known in the art, altering the carbon, nitrogen, and boron content in these systems effects their electrical and thermal properties, and each system can be adjusted to get an optimum stoichiometry and/or phase for a specific electrosurgery application. See for example, Kingery, W. D., Introduction to Ceramics, John Wiley & Sons, Inc., 1967.

The carbide ceramics, boride ceramics, nitride ceramics, and mixtures thereof of the present invention may be prepared by conventional methods including direct union of the elements at high temperatures (1600° C. and above for the carbides), and heating a compound of the metal, particularly the oxide, with carbon, boron or mixtures thereof. The carbides may also be prepared by heating the metal in the vapor of a suitable hydrocarbon. The borides may also be prepared by reacting the metals or their oxides with $B_2O_3$ and C, or with $B_4C$. This reaction results in the evolution of CO and the formation of the metal boride ceramic. Boron carbide ($B_4C$) may be prepared by the reduction of $B_2O_3$ with carbon in an electric furnace. These preparation methods are well known in the art and some such methods are described in Advanced Inorganic Chemistry, 5th Edition, F. A. Cotton and G. Wilkinson (1988).

The conducting ceramics may be formed into the required shapes for the electrosurgical instruments using convention ceramic processing techniques including injection molding, slip casting, cold pressing, hot pressing, and isostatic hot pressing (HIP).

In another embodiment of the invention a conducting ceramic may be formed by finely dispersing a carbide ceramic, boride ceramic, or nitride ceramic, or mixture thereof in a non-electrically conducting ceramic matrix. As an example, TiC particles (>25 weight %) may be uniformly dispersed in an $Al_2O_3$ matrix to yield a conducting ceramic. The proportion of the conducting ceramic and the uniformity of its dispersion in the non-conducting matrix must be controlled to ensure that the resulting material is a conducting ceramic. Examples of suitable non-conducting ceramics include $Al_2O_3$, MgO, $SiO_2$, silicates, $HfO_2$, BeO, and $TiO_2$. These ceramic composites may be prepared using standard techniques including slip casting, and hot pressing. The ceramic composites may be shaped into electrosurgical instruments using standard processing techniques including injection molding, slip casting, cold press and sinter, hot pressing, and isostatic hot pressing (HIP).

As described earlier, the conducting ceramic active electrode surface may be supported on a support means. In this case, the conducting ceramic may be formed on the support means using standard processing techniques including physical vapor deposition, chemical vapor deposition, sputter coating, laser deposition, flame spray, and plasma jet spray coating. If the support means is a metal core, the conductive ceramic active electrode surface may be formed as a coating on the surface of the support means by reacting the metal core with suitable carbon, boron, or nitrogen containing compounds. This procedure is described in detail below.

During use the active electrode surface is maintained at the desired electrical potential by a means for maintaining the active electrode surface at a desired electrical potential, as is well known in the art. See for example, U.S. Pat. Nos. 4,927,420 and 5,007,908, both of which are incorporated herein by reference.

CERMETS

Another class of materials that may be used in the present invention are cermets. These materials possess the same useful properties as the ceramics described above (good electrical and thermal conductivity and hardness) together with the additional advantage that they are less brittle that the pure ceramic. For this reason, in applications in which the electrosurgical instrument may have to operate under tensile loads, it will typically be desirable to fabricate the instrument out of cermet materials rather than ceramics.

Generally, any cermet that is substantially unreactive in the carburizing atmosphere of the electrosurgical procedure and that is capable of carrying sufficient current to perform electrosurgery may be used in the present invention. More particularly, cermets that may be used in the present invention include materials composed of one or more metals together with a carbide, boride, or nitride ceramic (or mixture thereof). Examples of suitable metals include Ag, Cu, Pt, Ta, V, Co, Ni, Fe, Mo, Ti, Hf, Zr, Nb, W and Al and examples of suitable ceramics include WC, TiC, $TiB_2$, TiN and $B_4C$.

The cermets of the present invention may be prepared using conventional methods including cold press and sintering, hot pressing, isostatic hot pressing, and molten metal infiltrating.

As in the case of the ceramics described above, the cermet material may be formed into electrosurgical instruments using conventional techniques including injection molding, slip casting, cold press and sinter, hot pressing, isostatic hot pressing, and molten metal infiltration.

The conducting cermet active electrode surface may be supported on a support means. In this case, the conducting cermet may be formed on the support means using standard processing techniques including physical vapor deposition, chemical vapor deposition, sputter coating, laser deposition, molten metal infiltration and plasma jet spray coating. If the support means is a metal core, the conductive cermet active electrode surface may be formed as a coating on the surface of the support means by reacting the metal core with suitable carbon, boron, or nitrogen containing compounds. This procedure is described in detail below.

$B_4C$-Al cermet (as well as WC-Co, WC-Ni-Fe, and TiC-Mo-Ni cermets) is especially well suited for use in electrosurgical instruments due to its high hardness, reaction resistance, and nontoxic components (B, C and Al). The by-products ($B_2O_3$, $Al_2O_3$ and $CO_2$) from reaction of the $B_4C$-Al cermet electrodes are more compatible with the human body than most other cermet and metal systems including the stainless steel and Teflon coated electrodes described above. $B_4C$-Al cermets have been demonstrated to work as effective electrosurgical instruments including Bovie blades, and bipolar forceps tips. Depending on the specific application, the composition of the $B_4C$-Al cermet is altered slightly, however, most compositions are within a range of 40 to 80 weight percent $B_4C$ and the remaining balance Al or an Al alloy. The composition and fabrication of $B_4C$-Al cermet systems are described in U.S. Pat. Nos. 4,605,440 and 4,718,941 both of which are incorporated herein by reference.

This cermet has also been shown to be compatible in magnetic resonance imaging (MRI) applications where most metal tools (stainless steel, steel, nickel, etc.) can not be used without distorting the image or causing safety hazards in the MRI environment. In preferred embodiments of the invention, the ceramic or cermet material forming the active electrode surface of the invention is of a type suitable for use in MRI applications (e.g., those in which the electrode is to be imaged by MRI).

Figure 1B:
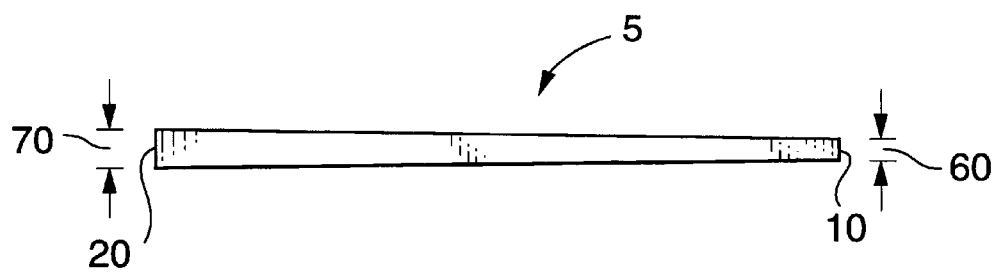
Figure 1C:
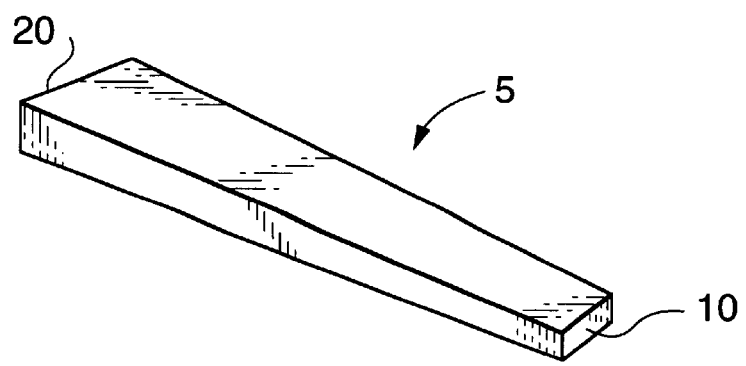

FIGS. 1a, 1b, and 1c show an example of a cermet Bovie Blade according to the present invention. FIG. 1a shows a top view of a Bovie blade 5 that includes a cutting tip 10 and an end 20 for attachment to a connector (not shown) and the power supply. In the embodiment shown, tip 10 has a width 30 of about 0.1 inches and end 20 has a width 40 of about 0.125 inches. The blade has a length 50 of about 1.25 inches. FIG. 1b shows a side view of the Bovie blade in which tip 10 has a thickness 60 of about 0.025 inches and end 30 has a thickness of about 0.035 inches. FIG. 1c shows a perspective top view of the Bovie blade 5. In the embodiment shown, the blade was made of $B_4C$-Al cermet which includes greater than 55% by weight of $B_4C$, is 99% dense, has all grains less than 50 microns diameter, and has an as-infiltrated condition that contains greater than 15% by weight unreacted Al.

CERAMIC OR CERMET COATED METAL CORED INSTRUMENTS

As discussed above, only the active electrode surface of an electrosurgical instrument need be made of the ceramics or cermets of the present invention. This allows for a large amount of latitude in designing an electrosurgical instrument with the optimal size, mechanical, electrical, and material characteristics. For example, an insulating support member may support electrodes made of the conducting ceramics or cermets of the present invention. Example of electrosurgical instruments including conducting electrodes (in these cases metal electrodes) supported on an insulating support means are described in U.S. Pat. Nos. 4,862,890, 4,958,539, 5,071,419, all of which are incorporated herein by reference. In another embodiment of the invention, a metal core may be coated with a conducting ceramic or cermet. This embodiment of the invention has many useful features that we now describe.

First, we note that many of the metals (W, Mo, Ti, Nb, Ta, Zr, Ni, Hf, Al, and V) and their alloys used to make the ceramics described above have relatively good tensile strengths. Therefore, by first forming a metal core and subsequently forming a carbide, boride, or nitride ceramic or mixture of these ceramics on the surface of the metal it is possible to prepare an electrosurgical instrument that retains the tensile strength of the metal core while improving the hardness and reaction resistance of the surface. The ceramic layer may be formed using conventional preparation techniques including heating the metal core in a carbon, boron, or nitrogen atmosphere or mixture of these atmospheres. For carbide ceramic or cermet coatings, the coating may also be formed by heating the metal core in a hydrocarbon atmosphere or carbon powder, and for boride ceramic or cermet coatings the coating may be formed by heating the metal core in boron powder (or a boron halide and hydrogen atmosphere). For nitride ceramic or cermet coatings the coating may be formed by heating the metal core in an ammonium or nitrogen atmosphere.

Using these preparation methods it is relatively easy to control the thickness of the ceramic layer deposited on the metal core. The ceramic layer must be thick enough that no metal is exposed during use of the instrument in electrosurgical procedures, but it should not be so thick as to lose the tensile strength advantages due to the metal core. Suitable ceramic layer thickness depends on the size and configuration of the instrument. Suitable thicknesses are from about 10 to 100 microns.

Carbide, boride, or nitride ceramic coatings, or mixtures of these ceramic coatings may also be applied by conventional coating techniques including physical vapor deposition, chemical vapor deposition, sputter coating, laser deposition, flame spray, and plasma jet spray coating. Such techniques increase the options available since the ceramic coating is not limited to include the same metal as the core. For example, a Tungsten Carbide coating may be applied to a Ti metal core to form an electrosurgical instrument, a Tungsten metal core may be plasma coated with Titanium Carbide, and diamond-like coatings may be deposited to a Titanium metal core.

Another advantage of the metal cored embodiment of the invention is due to the high thermal conductivity of the metal core. This results in the heating of the electrode surface being efficiently dissipated and this acts to further reduce the tissue build up during the electrosurgery.

Figure 2A:
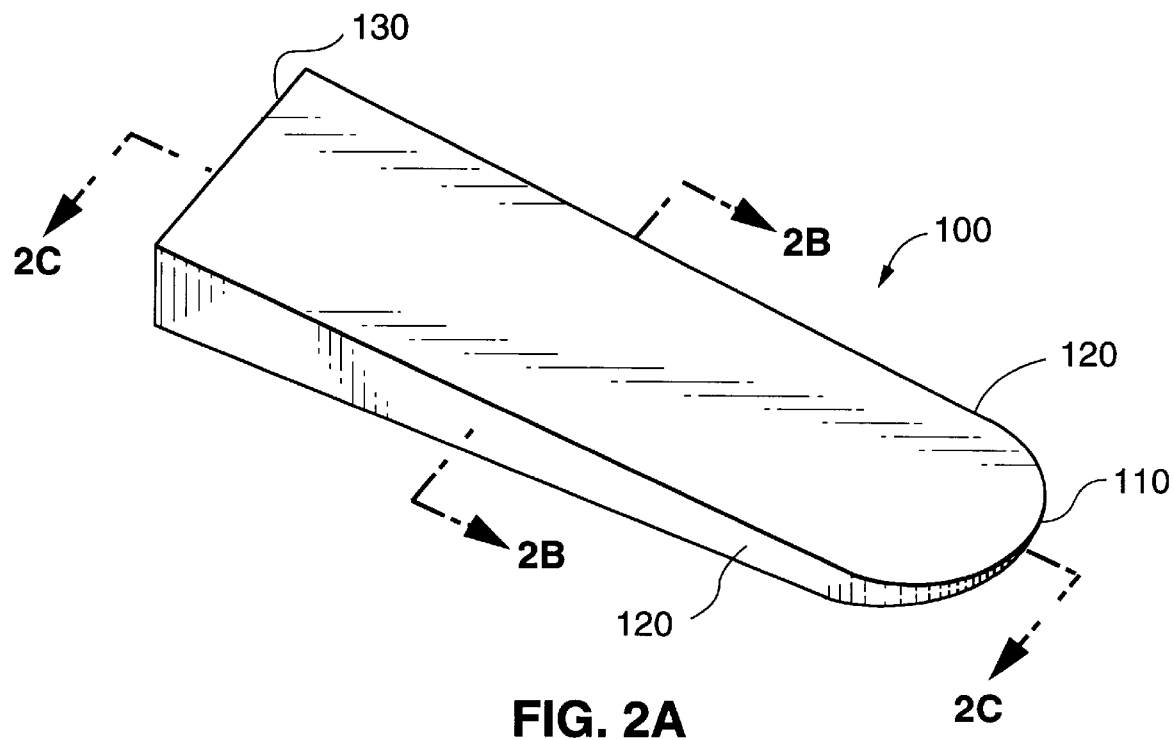
FIG. 2a is a perspective view of a metal cored electrosurgical instrument (a Bovie blade) according to the present invention.
Figure 2B:
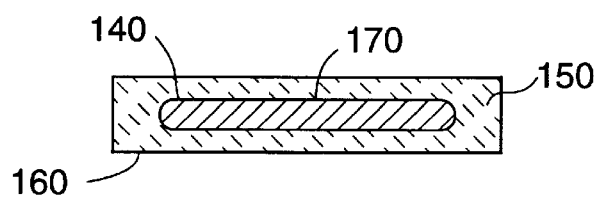
Figure 2C:
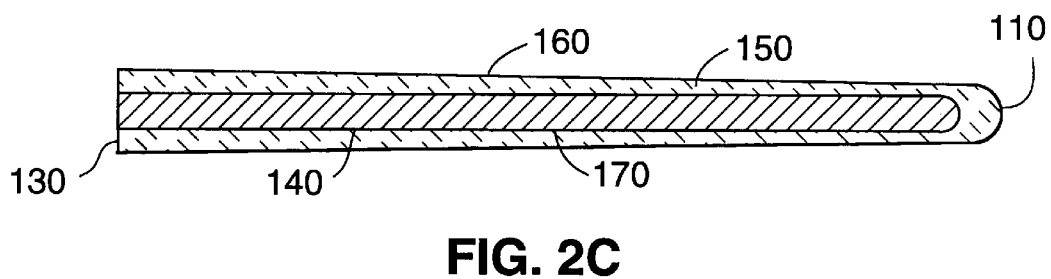

FIGS. 2a, 2b, and 2c show an example of an electrosurgical instrument (a Bovie blade) according to the present invention. The Bovie blade 100 includes cutting tip 1 10 and cutting edges 120, and an end 130 for attachment to a connector (not shown) and the power supply. The blade includes a metal core 140 coated with a conducting ceramic or cermet coating 150 having a surface 160.

There is an interface reaction zone 170 between the core 140 and the conducting ceramic or cermet coating 150. While the cutting tip and edges of the blade are made of a good electrically conducting cermet or ceramic, the center of the blade has a core 140 of high heat conduction metal like aluminum or aluminum alloy. The cutting tip and edges transfer heat to the core which then rapidly transfers this heat to an aluminum connector (not shown) and its surrounding environment. In variations on the FIG. 2 embodiment, Bovie blades similar to the one shown in FIG. 2 are made using one of several combinations of a metal core and a conducting ceramic coating (including carbide and/or boride coatings WC, MoC, TiC, $TiB_2$, and NbC) on the surface of a metal (W, Mo, Ti, and Nb) core. These combinations have been demonstrated to work as effective electrosurgical instruments.

Various modifications and variations of the described embodiments of the invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. An electrosurgical instrument, including an active electrode surface made of an electrically conducting ceramic or an electrically conducting cermet.

2. The electrosurgical instrument of claim 1, wherein the active electrode surface is made of a cermet selected from the group consisting of Aluminum/Boron Carbide, Cobalt/Tungsten Carbide, Nickel Iron/Tungsten Carbide, Nickel Molybdenum/Titanium Carbide, Titanium/Aluminum Oxide, and Aluminum/Aluminum Oxide.

3. The electrosurgical instrument of claim 1, further including means for maintaining the active electrode surface at a desired electric potential.

4. The electrosurgical instrument of claim 1, wherein the active electrode surface is made of an electrically conducting ceramic that is substantially unreactive in a carburizing environment present during electrosurgery.

5. The electrosurgical instrument of claim 1, wherein the active electrode surface is made of a cermet that is substantially unreactive in a carburizing environment present during electrosurgery.

6. The electrosurgical instrument of claim 1, wherein said electrosurgical instrument is a unipolar electrosurgical instrument.

7. The electrosurgical instrument of claim 1, wherein the active electrode surface is made of a cermet selected from the group consisting of Aluminum/Boron Carbide and an Aluminum Alloy/Boron Carbide.

8. The electrosurgical instrument of claim 7, wherein the cermet contains between about 40% and about 80% by weight of $B_4C$.

9. The electrosurgical instrument of claim 1, wherein the electrosurgical instrument further includes a support means for supporting the active electrode surface.

10. The electrosurgical instrument of claim 9, wherein the support means is a metal core and the active electrode surface is formed as a coating on a surface of the support means.

11. The electrosurgical instrument of claim 9, wherein the support means is an electrically insulating support means.

12. The electrosurgical instrument of claim 1, wherein the active electrode surface is made of a cermet.

13. The electrosurgical instrument of claim 12, wherein the cermet includes a refractory or transition metal.

14. The electrosurgical instrument of claim 12, wherein the cermet includes a metal selected from the group consisting of Silver, Hafnium, Copper, Platinum, Tantalum, Vanadium, Tungsten, Titanium, Zirconium, Niobium, Cobalt, Nickel, Iron, Molybdenum, and Aluminum.

15. The electrosurgical instrument of claim 12, wherein the cermet includes a second ceramic selected from the group consisting of carbide ceramics, boride ceramics, nitride ceramics, and mixtures of these ceramics.

16. The electrosurgical instrument of claim 1, wherein the active electrode surface is made of an electrically conducting ceramic comprising a first ceramic selected from the group consisting of carbide ceramics, boride ceramics, nitride ceramics, and mixtures of these ceramics.

17. The electrosurgical instrument of claim 16, wherein the first ceramic is selected from the group consisting of Boron Carbide, Tungsten Carbide, Titanium Carbide, Molybdenum Carbide, Niobium Carbide, Zirconium Carbide, Titanium Boride, Zirconium Boride, Vanadium Carbide, Hafnium Carbide, Titanium Nitride, Aluminum nitride, Zirconium nitride, and Tantalum Carbide.

18. The electrosurgical instrument of claim 16, wherein the conducting ceramic further comprises an electrically insulating ceramic.

19. The electrosurgical instrument of claim 18, wherein the first ceramic is dispersed in the electrically insulating ceramic.

20. An electrosurgical instrument, including a metal core coated with an active electrode surface made of an electrically conducting ceramic or an electrically conducting cermet.

21. The electrosurgical instrument of claim 20, wherein the active electrode surface is made of a cermet selected from the group consisting of Aluminum/Boron Carbide, Cobalt/Tungsten Carbide, Nickel Iron/Tungsten Carbide, Nickel Molybdenum/Titanium Carbide, Titanium Aluminum Oxide, and Aluminum/Aluminum Oxide.

22. The electrosurgical instrument of claim 20, wherein the cermet includes a metal component that is the same as the metal of the metal core.

23. The electrosurgical instrument of claim 20, further including means for maintaining the active electrode surface at a desired electric potential.

24. The electrosurgical instrument of claim 20, wherein the active electrode surface is made of an electrically conducting ceramic that is substantially unreactive in a carburizing environment present during electrosurgery.

25. The electrosurgical instrument of claim 20, wherein the active electrode surface is made of a cermet that is substantially unreactive in a carburizing environment present during electrosurgery.

26. The electrosurgical instrument of claim 20, wherein the active electrode surface is made of an electrically conducting ceramic comprising a diamond-like material.

27. The electrosurgical instrument of claim 20, wherein the active electrode surface is made of a cermet selected from the group consisting of an Aluminum/Boron Carbide or an Aluminum Alloy/Boron Carbide.

28. The electrosurgical instrument of claim 27, wherein the cermet contains between about 40% and about 80% by weight of $B_4C$.

29. The electrosurgical instrument of claim 20, wherein the active electrode surface is made of an electrically conducting ceramic comprising a first ceramic selected from the group consisting of carbide ceramics, boride ceramics, nitride ceramics and mixtures of these ceramics.

30. The electrosurgical instrument of claim 29, wherein the first ceramic is selected from the group consisting of Boron Carbide, Tungsten Carbide, Titanium Carbide, Molybdenum Carbide, Niobium Carbide, Zirconium Carbide, Titanium Boride, Zirconium Boride, Titanium Nitride, Aluminum Nitride, Zirconium Nitride, Vanadium Carbide, Hafnium Carbide, and Tantalum Carbide.

31. The electrosurgical instrument of claim 29, wherein the electrically conducting ceramic further includes a metal component that is the same metal as the metal core.

32. The electrosurgical instrument of claim 20, wherein the active electrode surface is made of a cermet comprising a metal and a second ceramic.

33. The electrosurgical instrument of claim 32, wherein the metal is a refractory or transition metal.

34. The electrosurgical instrument of claim 32, wherein the metal is selected from the group consisting of Silver, Copper, Hafnium, Platinum, Tantalum, Vanadium, Tungsten, Titanium, Zirconium, Niobium, Cobalt, Nickel, Iron, Molybdenum, and Aluminum.

35. The electrosurgical instrument of claim 32, wherein the second ceramic is selected from the group consisting of carbide ceramics, boride ceramics, nitride ceramics, and mixture of these ceramics.

* * * * *